(12) United States Patent
Xia et al.

(10) Patent No.: US 10,557,159 B2
(45) Date of Patent: Feb. 11, 2020

(54) METHOD OF CONVERTING RB TO RD BY USING CUTINASE UNDER STEPWISE CHANGING TEMPERATURES

(71) Applicants: Yongmei Xia, Wuxi (CN); Yun Fang, Wuxi (CN); Haijun Wang, Wuxi (CN)

(72) Inventors: Yongmei Xia, Wuxi (CN); Yun Fang, Wuxi (CN); Haijun Wang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 324 days.

(21) Appl. No.: 15/618,068

(22) Filed: Jun. 8, 2017

(65) Prior Publication Data

US 2018/0073049 A1 Mar. 15, 2018

(30) Foreign Application Priority Data

Sep. 12, 2016 (CN) .......................... 2016 1 0818205

(51) Int. Cl.
*C12P 19/56* (2006.01)
*C07H 15/24* (2006.01)

(52) U.S. Cl.
CPC .............. *C12P 19/56* (2013.01); *C07H 15/24* (2013.01); *C07B 2200/13* (2013.01)

(58) Field of Classification Search
None
See application file for complete search history.

(56) References Cited

U.S. PATENT DOCUMENTS

2014/0296499 A1* 10/2014 Chen ...................... C07H 15/24
536/18.1

* cited by examiner

Primary Examiner — Heidi Reese
(74) Attorney, Agent, or Firm — Lili Chen

(57) ABSTRACT

The present invention provides a method to produce RD by using a cutinase to catalyze the esterification of RB under stepwise cooling temperatures, which is related to the field of biosynthesis of organic compounds. The method uses a cutinase from *Thermobifida fusca* to catalyze the esterification of RB and sophorose to produce RD. The stepwise cooling temperatures are used to reduce the heat inactivation of the enzyme as well as to improve the mass transfer. The method catalyzes the esterification of RB to produce RD in a solvent such as methanol, DMSO and DMF. The reaction is safe, efficient and highly selective. In addition, the method uses stepwise additions of substrate RB and cooling temperatures for the esterification reaction. In this way, it speeds up the initial reaction rate, increases the amount of solved RB as it is converted to RD, and improves the mass transfer to further increase the reaction speed. In summary, the method uses moderate reaction conditions, and has a high yield and a simple purification procedure.

9 Claims, 4 Drawing Sheets

METHOD OF CONVERTING RB TO RD BY USING CUTINASE UNDER STEPWISE CHANGING TEMPERATURES

CROSS-REFERENCES AND RELATED APPLICATIONS

This application claims the benefit of priority to Chinese Application No. 201610818205.X, entitled "A method of converting RB to RD by using cutinase under stepwise temperature changes", filed Sep. 12, 2016, which is herein incorporated by reference in its entirety.

BACKGROUND OF THE INVENTION

Field of the Invention

The present invention provides a novel method to produce Rebaudioside D (RD) from Rebaudioside B (RB) by using cutinase to catalyze the conversion under stepwise temperature changes, which relates to the field of biosynthesis of organic compounds.

Description of the Related Art

Rebaudioside D, (4R)-13-[[2-O-(β-D-Glucopyranosyl)-3-O-(β-D-glucopyranosyl)-β-D-glucopyranosyl]oxy]kaur-16-en-18-oic acid 2-O-(β-D-glucopyranosyl)-β-D-glucopyranosyl ester, is a sweetener which exists in trace amounts in *stevia rebaudiana*. It has a texture and taste more similar to saccharose than Rebaudioside A (RA), which is currently used and could be obtained in large amounts. RD is usually used as a flour enhancer for RA as well as other sweeteners. RD was certified by GRAS as a trace substance in *stevia rebaudiana* in September 2010, and it also got certified as high-purity substance by GRAS in April 2015.

The main method to produce RD is phytoextraction, while chemical synthesis of RD has been rarely reported. The structure of RD is similar to RB, 13-O-[β-D-glucopyranosyl (1→2)-(β-D-glucopyranosyl(1→3))-β-D-glucopyranosyl]-ent-13-hydroxy-kaur-16-en-19-oic acid. RB is a steviol glycoside that could be made from RD by specific hydrolysis of the sophorosemoiety on C19 of RD. It is also a sweetener that exists in trace amounts in *stevia rebaudiana* (generally less than 0.1%). RB gives a bitter aftertaste and it can be produced by enzymatic or alkalic hydrolysis of glucose on C19 of RA. Hence, from the structural point of view, RD can be produced by esterification of sophorose with RB.

The esterification could be catalyzed by enzyme or acid. The acidic esterification is easy to conduct, in which the hydroxyl groups in RB should be protected to avoid the esterification between RB molecules. Acetylation is a well-known method to protect the hydroxyl group, and is used to protect the saccharide hydroxyl in sucralose synthesis. The enzymatic esterification is more gentle and specific than chemocatalysis. If esterification between RB and sophorose can be conducted specifically, the protection and deprotection step can be avoided. The enzymatic synthesis of glycolipid is commonly reported. There are more than 10 types of popular commercial lipases, and the most popular lipase is Novazym435. For example, Novazym435 catalyzes the reaction between lauric acid and sucrose in tertiary butanol to produce sucrose monolaurate and sucrose dilaurate. As another example, Novazym435 can catalyze the synthesis of trehalose. Enzymes from different sources have different substrate selectivity for the chain length of the acylating reagents. Enzymes from multiple sources of bacteria and fungus could catalyze glucose monoester reaction, for example, the *pseudomonas* and fungus's enzymatic activity with the carbon source in culture media is outstanding. But RB is an acid with 3 glucose residues, which is different with the aliphatic acids mentioned above. After screening more than twenty commercial lipases, none of the lipases can catalyze the sophorose esterification onto RB. This may be due to the solubility issue of RB and the steric hindrance of hydroxyl on RD. In addition, the solvent of RB always has a remarkable inhibitory effect to lipases, which made it difficult to perform enzymatic esterification by lipases.

DETAILED DESCRIPTION

The first goal of the present invention is to provide a novel method to produce RD by using cutinase to catalyze the esterification between RB and sophorose under controlled temperatures, which had advantages such as high conversion rate, fast speed, high selectivity, and easy purification.

This method uses a cutinase from *Thermobifida fusca* to catalyze the esterification between RB and sophorose under a programmed cooling condition.

The reaction equation of catalytic esterification between RB and sophorose which uses the cutinase from *Thermobifida fusca* to obtain RD is shown below.

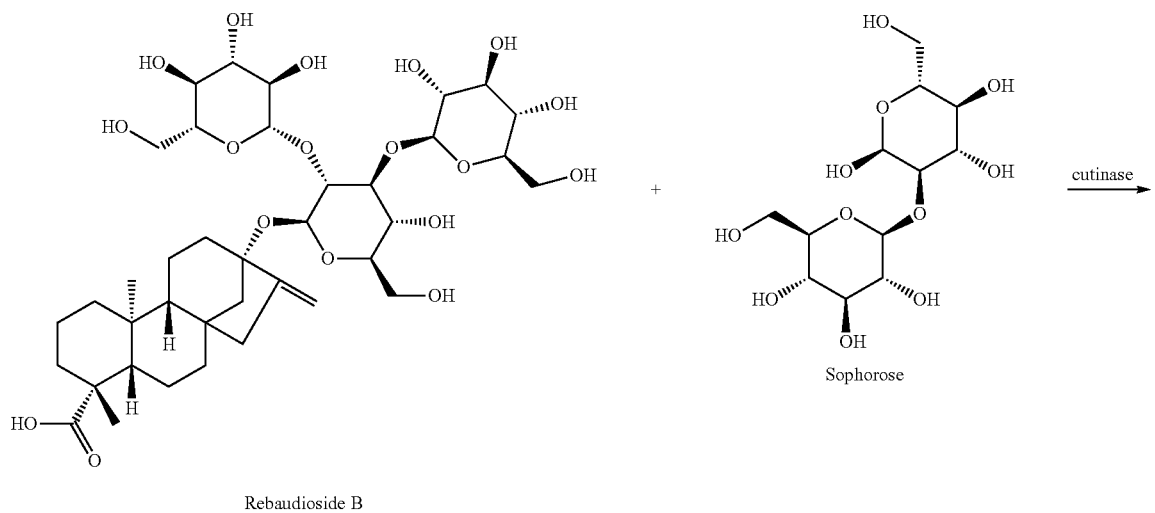

Rebaudioside B

Sophorose

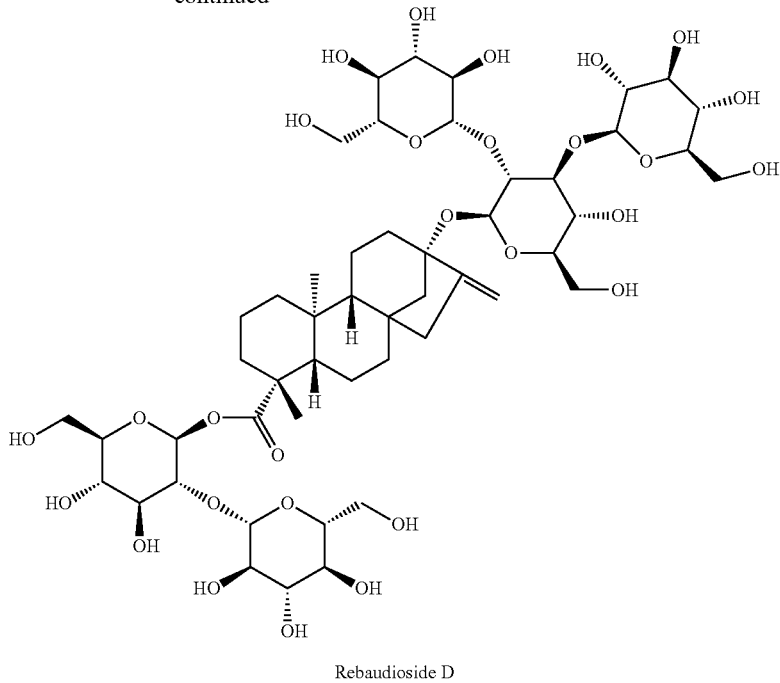

Rebaudioside D

The method comprises the following steps:
(1) RB is dissolved in a solvent to 10-20 g/L together with sophorose to make a substrate mixture, the amount of sophorose is stoichiometric to total RB;
(2) the cutinase from *Thermobifida fusca* is added to the substrate at 55° C.;
(3) the mixture obtained from step (2) is stirred well and heated up to 70° C. and reacted for 0.5-1 hr;
(4) 10-20 g/L RB is replenished and the reaction continues at 60° C. for 1-1.5 hr;
(5) 30-50 g/L RB is replenished and the reaction continues at 60° C. for 2-6 hr.

In one embodiment of the present invention, the cutinase used can be an enzyme solution, powdered or immobilized enzyme. The cutinase can be obtained physically, chemically or biologically. For example, the cutinase could be immobilized on resins, or connected with magnetic beads through affinity adsorption.

In one embodiment of the present invention, the solvent mentioned above is selected from one or more of methyl alcohol, dimethyl sulfoxide and dimethylformamide with pH 6.0 phosphate buffer. The quantity of pH 6.0 phosphate buffer was 0.1%-0.05% of the quantity of organic solvent.

In one embodiment of the present invention, the dosage of the enzyme is 100-500 U/g RB.

In one embodiment of the present invention, when the reaction is finished, the solvent is removed by vacuum distillation and then the remaining mixture is recrystallized in aqueous methanol solution (90%) for 2-3 times to obtain the white crystal RD.

In one embodiment of the present invention, when 60% RB is converted to RD at 60° C., 4A molecular sieve is added to remove water. When RB conversion rate reaches 70%-78%, the solvent is removed by vacuum distillation and then the remaining mixture is recrystallized in aqueous methanol solution (90%) for 2-3 times to obtain white crystal RD.

The cutinase (EC3.1.1.74) is a α/β hydrolase, belonging to serine esterases, which could degrade cutin to generate fatty acids. The cutinase can hydrolyze not only the easter bonding of the infusibility polymeric plant cutin, but also the long-chain or short-chain fatty acid esters, emulsive triglyceride and dissoluble synthesized esters. Therefore, it is a multifunctional lyase. Compared with other lipases, the cutinase's cellulose binding domain made it more effective in association with cellulose, polysaccharide and oligos.

The advantages of the present invention include:
(1) This invention provides a novel method to produce RD.
(2) The present method could catalyze RB to produce RD in solvents like methanol, DMSO, DMF and so on. The reaction is safe, efficient and highly selective.
(3) The esterification is proceeded under programmed cooling temperatures, wherein the generated RD could increase the solubility of RB. Both of the mass transfer speed and the reaction speed are increased at the same time.
(4) In summary, the present method for producing RD performs under moderate reaction conditions, has a high yield and an easy purification procedure.

DESCRIPTION OF THE PREFERRED EMBODIMENTS

RD detection method: the modified JECFA (Steviol Glycosides INS No. 960) method is used, and the samples are tested by HPLC.

Chromatographic condition: C18 column, 4.6×250 mm, acetonitrile 31.3% (use phosphate to regulate the pH to 2.6), isocratic elution, the flow rate at 1 mL/min, carbon column temperature at 40° C., UV detection wavelength of 210 nm, and the inlet sample volume is 10 μL.

The equation for calculating RD conversion:

$$RB(\%) = \frac{C_0 - C(RB)}{C_0} \quad (1)$$

$C_0$—RB's initial concentration
C(RB) the remaining RB's concentration after reaction
RB's quality fraction is calculated by the equation below (refer to the 2014 Chinese standard GB 8270-2014):

$$w_R = \frac{m_R}{m} \times \frac{A_a}{A_R} \times 100\% \quad (2)$$

$m_R$—the dry weight of Rebaudioside A in the Rebaudioside A standard solution, the unit is milligram (mg);
m—the dry weight of the samples in the solution, the unit is milligram (mg);
$A_a$—the chromatogram peak area of the Rebaudioside A in the samples;
$A_R$—the chromatogram peak area of the Rebaudioside A in the Rebaudioside A standard solution.

The mass fraction of RB or RD is calculated by the equation below:

$$w_i = \frac{m_s}{m} \times \frac{f_i \times A_i}{A_s} \times 100\% \quad (3)$$

i—stands for RB or RD;
$m_s$—the dry weight of stevioside in the stevioside standard solution, the unit is mg;
$f_i$—the ratio of the i composition and stevioside formula weight: the $f_i$ of RD is 1.40;
$A_i$—the chromatogram peak area of the i composition in the samples;
$A_s$—the chromatogram peak area of stevioside in the stevioside standard solution.

The cutinase was produced according to the method described in the Chinese patent titled "A kind of high-temperature resistant cutinase and its gene sequence" with the patent number of ZL200810020124.0.

EXAMPLES

Example 1

Figure 1:
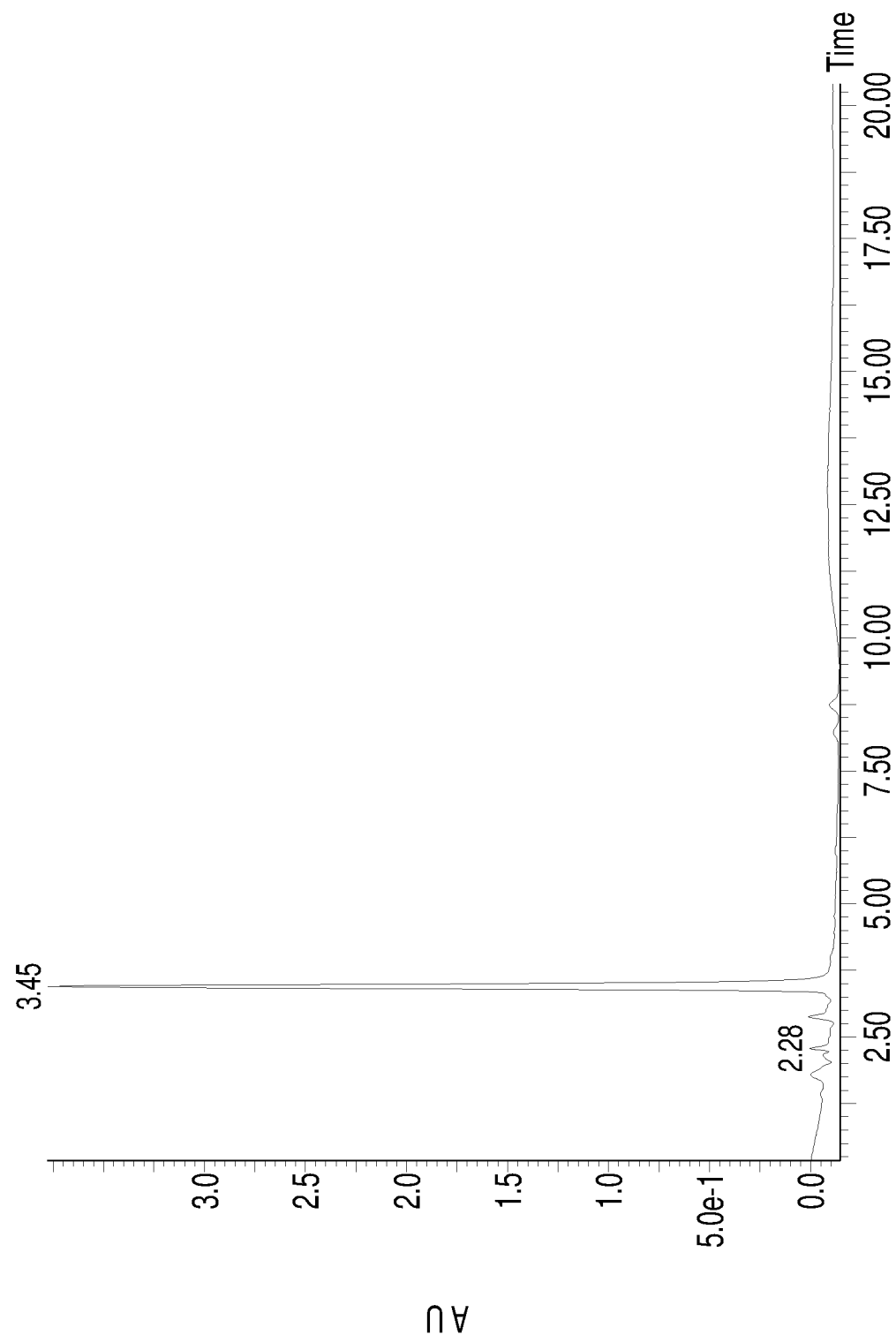
FIG. 1. HPLC chromatogram of RD standard sample.
Figure 2:
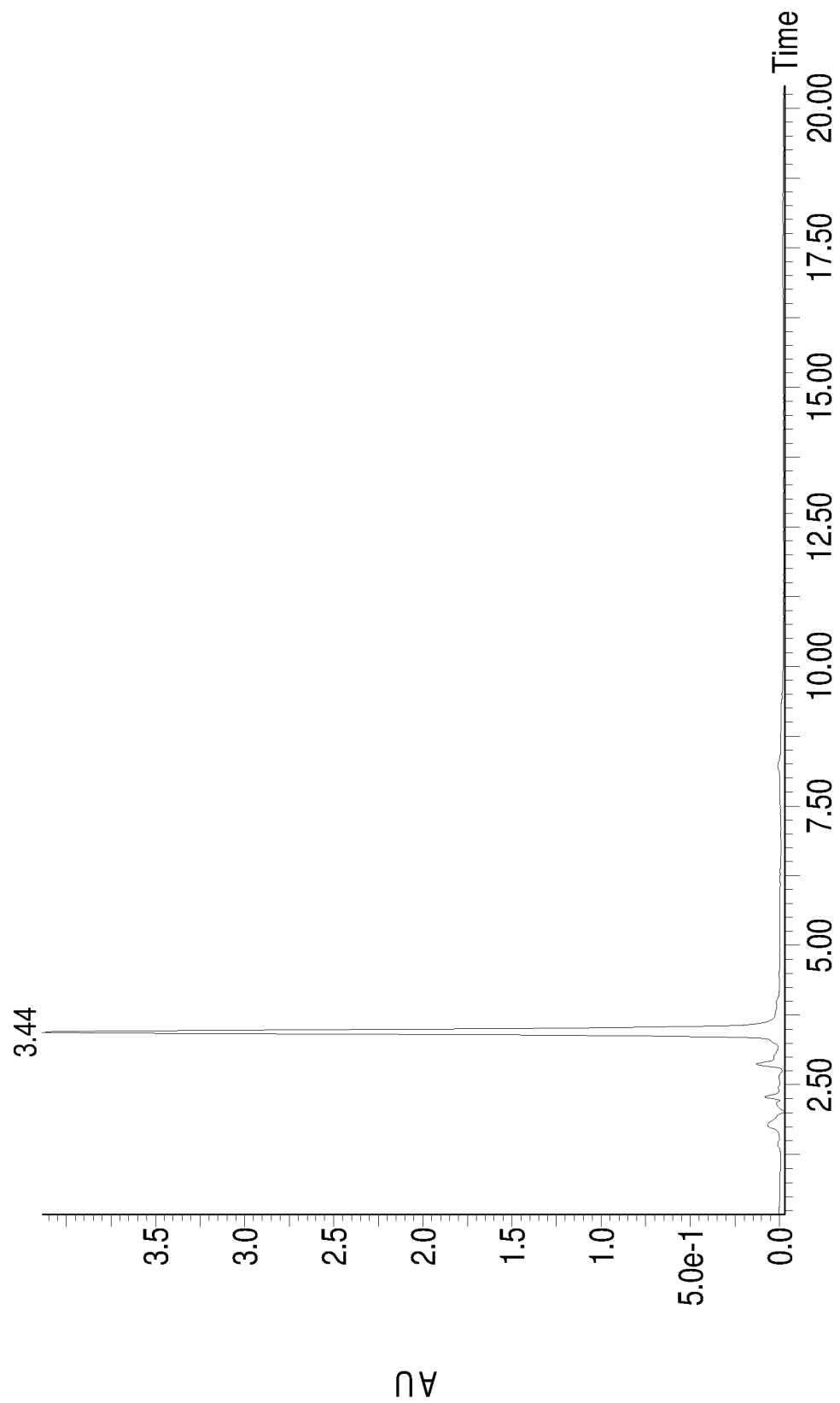
FIG. 2. HPLC chromatogram of RD produced in Example 1.
Figure 3:
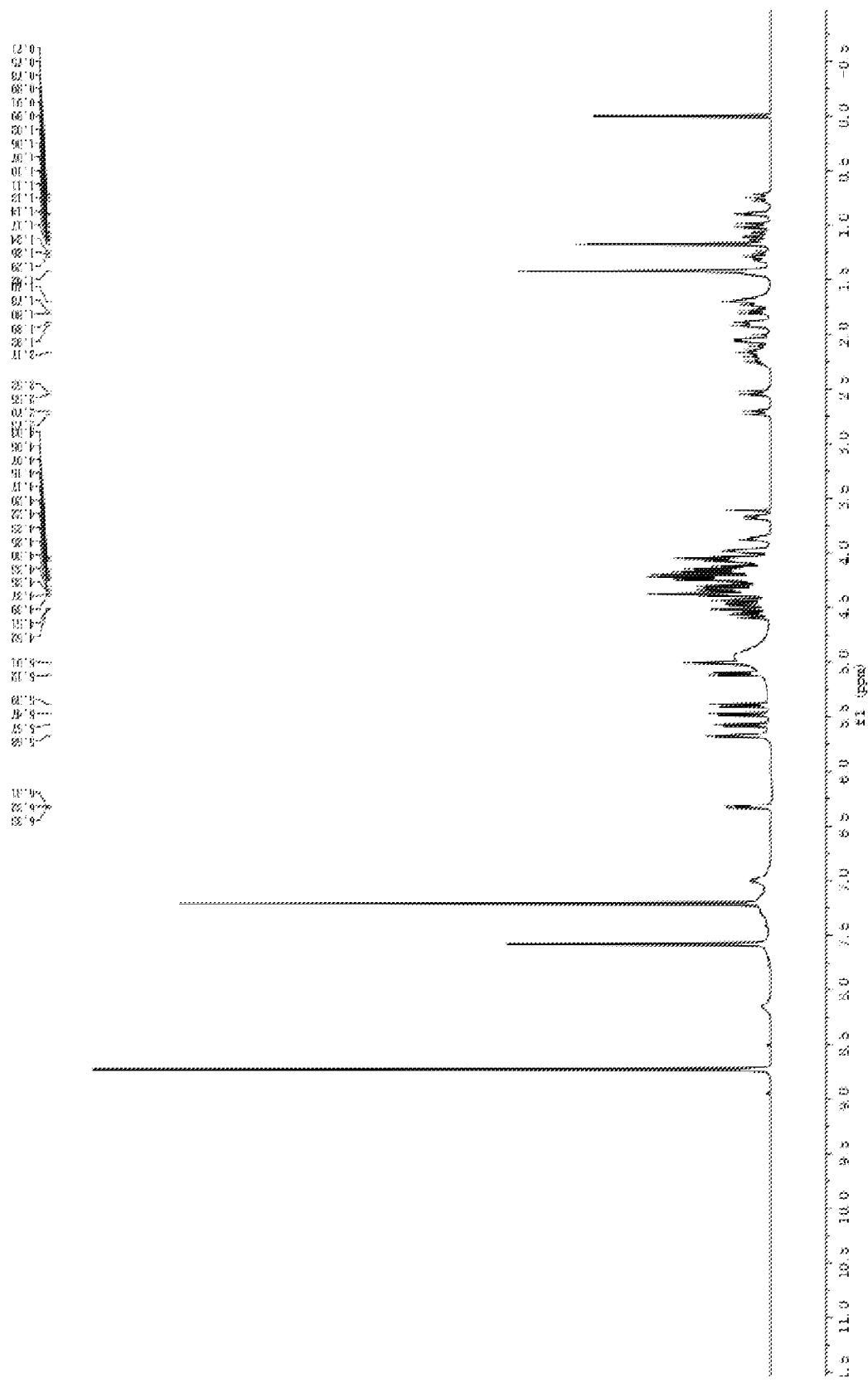
FIG. 3. $^1$H NMR chromatogram of RD produced in Example 1.
Figure 4:
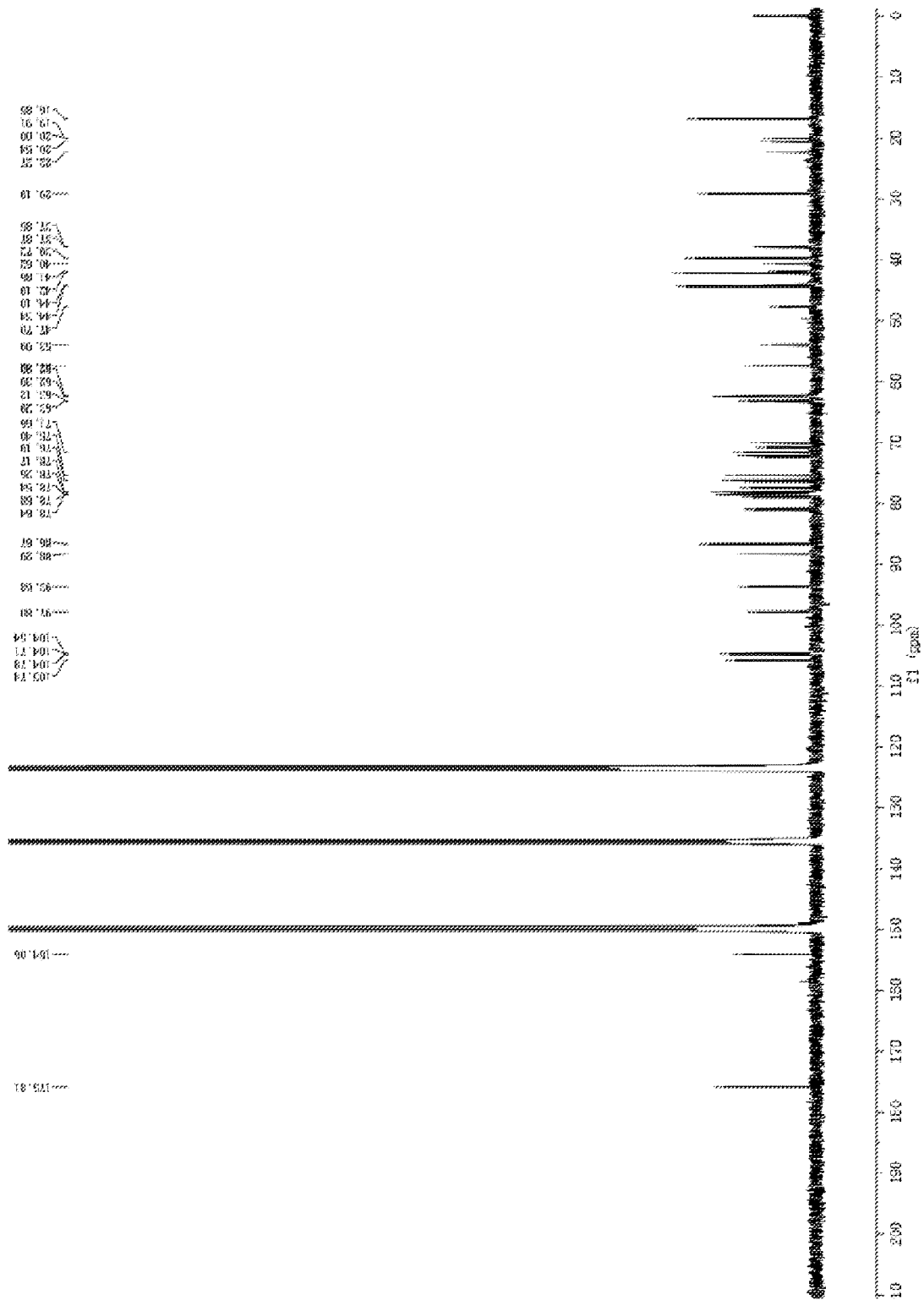
FIG. 4. $^{13}$C NMR chromatogram of RD produced in Example 1.

RB was dissolved in dimethyl sulfoxide (DMSO) containing 0.03% (w/w) pH 6.0 phosphate buffer to 10 g/L together with sophorose (stoichiometric to total RB), and 400 U/g cutinase from *Thermobifida fusca* was added to the substrate at 55° C. The mixture obtained above was well mixed and heated up to 70° C. to react for 0.5-1 hr. 20 g/L RB was then replenished and the reaction was continued at 60° C. for another 1 hr, and another 50 g/L RB was replenished and the reaction was continued at 60° C. for 10 hr. After that, 4A molecular sieve was used to remove water, and the solvent was removed by vacuum distillation. The remaining mixture was recrystallized in aqueous methanol solution (90%) for 2-3 times to obtain the white crystal RD. The mass spectrometric data of the product is shown in Table 1, which indicates that the final product is RD. HPLC chromatogram of the final product (see FIG. 2) indicates that RD produced by this method is in high purity. The final yield of RD was 56% and the purity was 95.7%.

TABLE 1

The mass spectrometric data of the production

| Sugar | position | $^1$H NMR | $^{13}$C NMR |
|---|---|---|---|
| | 1 | 0.75t, 1.90d | 40.6 |
| | 2 | 1.72t, 2.19m | 20.0 |
| | 3 | 1.00td, 2.72d | 37.9 |
| | 4 | — | 44.3 |
| | 5 | 1.10td | 57.5 |
| | 6 | 2.03d, 2.53d | 22.3 |
| | 7 | 1.29dd, | 41.9 |
| | 8 | — | 42.2 |
| | 9 | 0.90d | 54.0 |
| | 10 | — | 39.7 |
| | 11 | 1.72t, 1.79d | 20.5 |
| | 12 | 2.03t, 2.19m | 37.8 |
| | 13 | — | 86.7 |
| | 14 | 1.90d, 3.67m | 44.1 |
| | 15 | 2.19m | 47.7 |
| | 16 | — | 154.1 |
| | 17 | 5.01s, 5.68s | 104.5 |
| | 18 | 1.17s | 29.2 |
| | 19 | — | 175.8 |
| | 20 | 1.42s | 16.9 |
| I | 1' | 6.32m | 93.7 |
| | 2' | 4.21m | 81.2 |
| | 3' | 4.21m | 77.5 |
| | 4' | 4.21m | 70.9 |
| | 5' | 3.98 | 78.2 |
| | 6' | 4.35m, 4.35m | 62.2-63.4 |
| II | 1" | 5.11d | 97.8 |
| | 2" | 4.35m | 80.9 |
| | 3" | 4.21m | 88.3 |
| | 4" | 4.08m | 70.0 |
| | 5" | 3.97m | 78.0 |
| | 6" | 4.21m, 4.51m | 62.2-63.4 |
| III | 1''' | 5.58d | 104.7 |
| | 2''' | 4.21m | 76.5 |
| | 3''' | 4.35m | 78.3-79.0 |
| | 4''' | 4.21m | 72.4 |
| | 5''' | 3.98m | 78.3-79.0 |
| | 6''' | 4.35m, 4.51m | 62.2-63.4 |
| VI | 1'''' | 5.40d | 105.7 |
| | 2'''' | 4.08m | 76.2 |
| | 3'''' | 4.35m | 78.3-79.0 |
| | 4'''' | 4.08m | 72.2 |
| | 5'''' | 4.21m | 78.3-79.0 |
| | 6'''' | 4.21m, 4.51m | 62.2-63.4 |
| V | 1''''' | 5.48d | 104.7 |
| | 2''''' | 4.21m, | 75.4 |
| | 3''''' | 4.35m | 78.3-79.0 |
| | 4''''' | 4.08m | 71.6 |
| | 5''''' | 4.08m | 78.3-79.0 |
| | 6''''' | 4.21m, 4.51m | 62.2-63.4 |

Example 2

RB was dissolved in DMF containing 0.06% (w/w) pH 6.0 phosphate buffer to 20 g/L together with sophorose (stoichiometric to total RA), and 100 U/g cutinase from *Thermobifida fusca* was added to the substrate at 55° C. The mixture obtained above was mixed well and heated up to 70°

C. to react for 1 hr. 20 g/L RB was replenished and the reaction was continued at 60° C. for 1 hr, and 30 g/L RB was replenished and the reaction was continued at 60° C. for 15 hr. 4A molecular sieve was used to remove water, and the solvent was removed by vacuum distillation. The remaining mixture was recrystallized in aqueous methanol solution (90%) for 3 times to obtain the white crystal RD. The production yield of RD was 49.1% and purity was 98.7%.

Example 3

RB was dissolved in methanol containing 0.3% (w/w) pH 6.0 phosphate buffer to 20 g/L together with sophorose (stoichiometric to total RA), and 30 U/g RB cutinase from *Thermobifida fusca* was added to the substrate at 55° C. The mixture obtained above was well mixed and heated up to 70° C. to react for 1 hr. 20 g/L RB was replenished and the reaction was continued at 60° C. for 1 hr. RB was replenished again with 30 g/L and the reaction was continued at 60° C. for 10 hr. 4A molecular sieve was used to remove water, and the solvent was removed by vacuum distillation. The remaining mixture was recrystallized in methanol solution (90%) 3 times to get the white RD. The production yield of RD was 50.2% and purity was 98.4%.

Example 4

This is a comparison example without stepwise changing temperatures.

RB was dissolved in methanol containing 0.3% (w/w) pH 6.0 phosphate buffer to 20 g/L together with sophorose (stoichiometric to total RA), and 400 U/g RB cutinase from *Thermobifida fusca* was added to the substrate at 55° C. The mixture obtained above was well mixed and heated up to 70° C. to react for 0.5 hr. 20 g/L RB was replenished and the reaction was continued at 70° C. for 1 hr, and then 30 g/L RB was replenished and the reaction was continued at 70° C. for 12 h. 4A molecular sieve was used to remove water, and the solvent was removed by vacuum distillation. The remaining mixture was recrystallized in methanol solution (90%) 2 times to get the white RD. The final yield of RD was 30.6% and purity was 94.8%.

Example 5

This is a comparison example without multiple additions of substrate RB.

RB was dissolved in methanol containing 0.3% (w/w) pH 6.0 phosphate buffer to 80 g/L together with sophorose (stoichiometric to total RA), and 400 U/g RB cutinase from *Thermobifida fusca* was added at 55° C. The mixture obtained above was well mixed and heated up to 70° C. to react for 15 hr. 4A molecular sieve was used to remove water, and the solvent was removed by vacuum distillation. The remaining mixture was recrystallized in methanol solution (90%) 3 times to get the white RD. The final yield of RD was 31.0% and the purity was 96.8%.

Comparison of the results in Examples 1-3 and Examples 4-5 shows that the stepwise cooling temperatures used in the production of RD can significantly increase the final yield.

\* \* \*

While the invention has been described in some details for the preferred embodiments, it is not intended to act as a limitation for the invention. One skilled in the art will appreciate that various changes in form and detail can be made without departing from the true scope of the invention. The scope of the invention should be only defined by the claims. All figures, tables, appendices, patents, patent applications and publications, referred to above, are hereby incorporated by reference.

What is claimed is:

1. A method for producing Rebaudioside D (RD) from Rebaudioside B (RB), wherein said method uses a cutinase to catalyze the esterification of RB and sophorose to produce RD under temperatures which are reduced stepwise.

2. The method of claim 1, wherein the reaction equation of esterification of RB to produce RD is shown below:

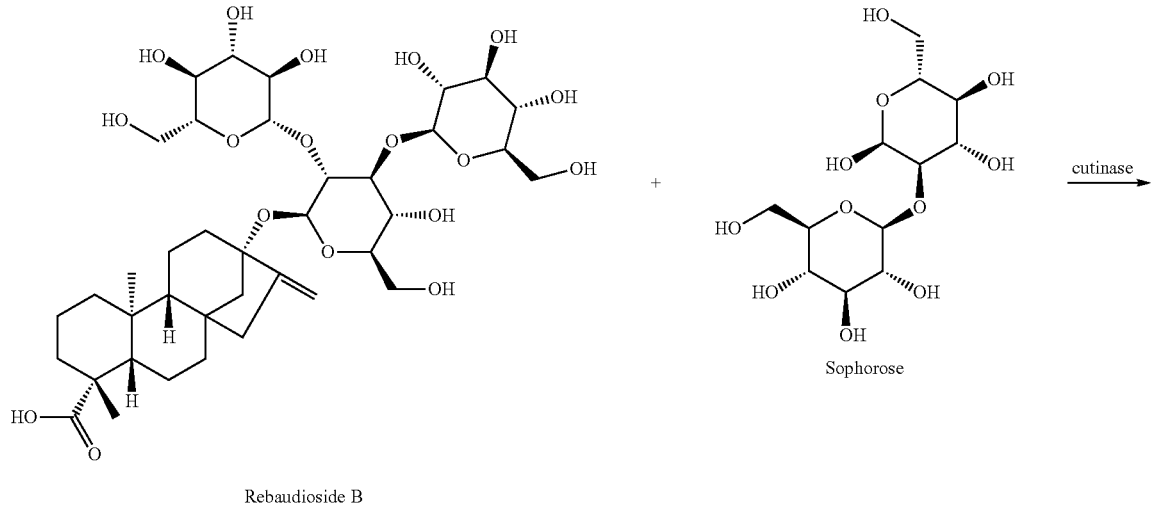

-continued

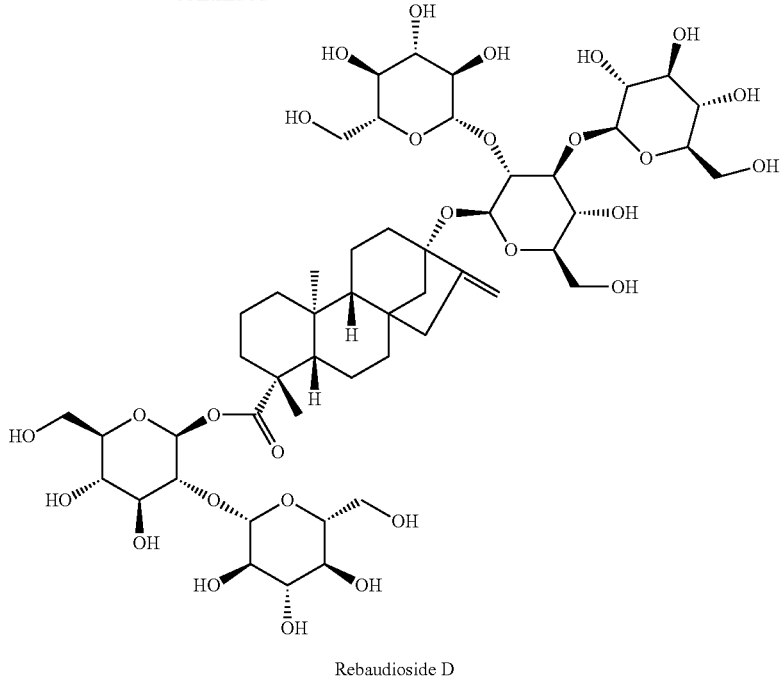

Rebaudioside D

3. The method of claim 1, comprises the following steps:
(1) dissolving substrate RB in a solvent to achieve a concentration of 10-20 g/L;
(2) adding the cutinase to the substrate at 55° C. to obtain a reaction mixture;
(3) mixing well the reaction mixture obtained from step (2) and heating it up to 70° C. to react for 0.5-1 hour;
(4) replenishing the reaction mixture to maintain a concentration of 10-20 g/L RB and continuing the reaction at 60° C. for 1-1.5 hours; and
(5) replenishing the reaction mixture again to achieve and maintain a concentration of 30-50 g/L RB and continuing the reaction at 60° C. for 2-6 hours.

4. The method of claim 1, wherein the added cutinase is selected from an enzyme solution, enzyme powder, and immobilized enzyme.

5. The method of claim 4, wherein the cutinase is obtained by physical, chemical or biological methods.

6. The method of claim 3, wherein said solvent is selected from one or more of the group consisting of methanol, dimethyl sulfoxide, and dimethylformamide, wherein the solvent contains 0.03%-0.3% (w/w) pH 6.0 phosphate buffer.

7. The method of claim 3, wherein the dosage of said cutinase is 100-500 U/g RB.

8. The method of claim 3, wherein, after said reaction is finished, the solvent is removed by vacuum distillation and the remaining reaction product is recrystallized in an aqueous methanol solution (90%) for 2-3 times to obtain RD as white crystals.

9. The method of claim 3, wherein, when 60% RB is converted to RD at 60° C., 4A molecular is added to remove water; when RB conversion rate reaches 70%-78%, the solvent is removed by vacuum distillation and the remaining reaction product is recrystallized in an aqueous methanol solution (90%) for 2-3 times to obtain RD as white crystals.

* * * * *